United States Patent
Liu et al.

(10) Patent No.: US 9,249,437 B2
(45) Date of Patent: Feb. 2, 2016

(54) PROCESS FOR PREPARING BIODIESEL FROM RENEWABLE OIL AND FAT CATALYZED BY LIPASE WITH ONLINE DEHYDRATION

(75) Inventors: Dehua Liu, Beijing (CN); Wei Du, Beijing (CN); Xuebing Zhao, Beijing (CN); Luole Zhu, Beijing (CN)

(73) Assignee: Tsinghua University, Beijing (CN)

( * ) Notice: Subject to any disclaimer, the term of this patent is extended or adjusted under 35 U.S.C. 154(b) by 0 days.

(21) Appl. No.: 13/883,747

(22) PCT Filed: Nov. 4, 2011

(86) PCT No.: PCT/CN2011/081784
§ 371 (c)(1),
(2), (4) Date: Jun. 12, 2013

(87) PCT Pub. No.: WO2012/059065
PCT Pub. Date: May 10, 2012

(65) Prior Publication Data
US 2013/0260428 A1    Oct. 3, 2013

(30) Foreign Application Priority Data
Nov. 4, 2010    (CN) .......................... 2010 1 0536576

(51) Int. Cl.
*C12P 7/64*    (2006.01)
*C10L 1/02*    (2006.01)

(52) U.S. Cl.
CPC ................. *C12P 7/649* (2013.01); *C10L 1/026* (2013.01); *C10L 2200/0476* (2013.01); *C10L 2290/08* (2013.01); *C10L 2290/26* (2013.01); *C10L 2290/542* (2013.01); *C10L 2290/548* (2013.01); *Y02E 50/13* (2013.01)

(58) Field of Classification Search
None
See application file for complete search history.

(56) References Cited

FOREIGN PATENT DOCUMENTS

| | | | |
|---|---|---|---|
| CN | 1687313 A | | 10/2005 |
| CN | 1888020 A | | 1/2007 |
| CN | 101113360 A | * | 1/2008 ............... C10G 3/00 |
| CN | 101838670 A | | 9/2010 |
| CN | 102021207 A | | 4/2011 |

OTHER PUBLICATIONS

CN 101113360A English Translation by Google (last viewed on Sep. 23, 2014).*
Tan et al., Biodiesel production with immobilized lipase: A review., Biotechnology Advances (Epub May 24, 2010), vol. 28, Issue 5, pp. 628-634.*
International Search Report for PCT Application No. PCT/CN2011/081784, mailed Jan. 19, 2012.
Written Opinion for PCT Application No. PCT/CN2011/081784, mailed Jan. 19, 2012.

* cited by examiner

*Primary Examiner* — Alexander Kim

(57) ABSTRACT

Disclosed is a process for preparing biodiesel from renewable oil and fat catalyzed by lipase with online dehydration. The method uses a short chain alcohol ROH as an acyl-acceptor, and utilizes a lipase as the catalyst to catalyze transesterification reaction of oil and fat feedstock with said short chain alcohol, so as to synthesize biodiesel; and online dehydration with a membrane or a molecular sieve is carried out during the whole process or part of the reaction process. Such online dehydration process greatly simplifies the operation procedure, and provides good economic and environmental benefits.

10 Claims, 1 Drawing Sheet

PROCESS FOR PREPARING BIODIESEL FROM RENEWABLE OIL AND FAT CATALYZED BY LIPASE WITH ONLINE DEHYDRATION

TECHNICAL FIELD

The present invention belongs to the technical field of biofuel synthesis. Specifically, the present invention relates to a process for preparing biodiesel from renewable oil and fat catalyzed by lipase with online dehydration.

BACKGROUND

Biodiesel, which is new prospect in oil and fat industry, are long-chain fatty acid ester substances generated by transesterification reaction of biological oil and fat feedstock. It is a novel renewable energy resource without pollution, and is referred to as biodiesel. The combustion properties of it are comparable to the traditional petroleum diesel. Since the harmful substances in the exhaust emitted from an engine in which biodiesel is combusted is 50% reduced when compared to traditional petroleum diesel, extensive attention has recently been drawn to the investigations and applications of biodiesel.

Currently, biodiesel is primarily produced by chemical processes, i.e. using animal/plant oil and fat together with some low carbon alcohols (methanol or ethanol) to conduct transesterification reaction under the catalysis of acidic or alkaline catalysts, so as to generate corresponding fatty acid methyl ester or ethyl ester. There exist the following inevitable disadvantages when using chemical processes to prepare biodiesel: (1) the free fatty acids and water in the oil and fat feedstock severely affect the progression of the reaction; (2) the poor solubility of methanol in oil and fat would easily result in the formation of emulsion, such that the subsequent processing procedure will become complicated; and (3) the amount of methanol used according to the requirements of the process greatly exceeds the molar ratio of the reaction, and the recovery of the excess methanol increases the energy consumption during the process.

A process using a biological enzyme for synthesizing biodiesel has the following advantages: mild reaction conditions, no pollutant emitted, and broad applicability for various oil and fat feedstock. Such process is in accordance with the green chemistry trend, and thus is getting increasing attention. However, in conventional lipase-catalyzing processes of converting oil and fat feedstock for the preparation of biodiesel, when the water content in the oil and fat feedstock is greater than 0.5% (based on the weight of the oil), the acid value of the biodiesel product after the reaction is generally higher than 0.5 mg KOH per gram of oil. This does not fulfill the acid value standard required for China and International biodiesel quality, and thus subsequent processing procedure involving complicated alkaline neutralization is required afterwards. Such subsequent processing procedure using alkaline neutralization to decrease the acid value affects the yield of the product, and brings about pollution problems.

CONTENT OF THE INVENTION

The purpose of the invention is to provide a process for preparing biodiesel from renewable oil and fat catalyzed by lipase with online dehydration. During the processes in which lipase is used to catalyze renewable oil and fat feedstock to prepare biodiesel, online dehydration is employed, so that the fatty acid content in the final biodiesel product is higher than 98%, and the acid value is less than 0.5 mg KOH per gram of oil. Said lipase reaction can be accomplished in a single step, and can also be accomplished in multiple steps. In the single-step or multiple-step reaction process of lipase catalysis, the acid value of the final biodiesel product can be less than 0.5 mg KOH per gram of oil by introducing online dehydration during the whole process or part of the process. Such online dehydration process greatly simplifies the operation procedure, and provides good economic and environmental benefits. The schematic diagram for conducting online dehydration in single-step lipase catalysis process is shown in FIG. 1, and the schematic diagram for conducting online dehydration in multiple-step lipase catalysis process is shown in FIG. 2.

In the present invention, a short chain alcohol ROH is used as an acyl-acceptor, and a lipase is utilized as the catalyst to catalyze transesterification reaction of oil and fat feedstock with said short chain alcohol, so as to synthesize biodiesel. The lipase reaction can be accomplished in a single step, and can also be accomplished in multiple steps. In the single-step or multiple-step reaction process of lipase catalysis, the acid value of the final biodiesel product can be less than 0.5 mg KOH per gram of oil by introducing online dehydration during the whole process or part of the process.

The present invention is characterized in that, 4-8 mole of short chain alcohol based on the mass of oil and fat and 20-2000 units of lipase based on the mass of oil and fat are added into single-stage or multi-stage reactor, and online dehydration with a membrane or a molecular sieve is carried out during the whole process or part of the reaction process; the temperature is maintained at 20-50° C.; after 3-10 hours, the yield for converting oil and fat feedstock into biodiesel is greater than 98%, and the acid value of the final biodiesel product is less than 0.5 mg KOH per gram of oil.

The online dehydration with a membrane or a molecular sieve carried out during the whole process refers to that an online dehydration with a membrane or a molecular sieve is carried out during the whole process or part of the reaction process of enzyme catalysis.

The membrane is organic membrane, inorganic membrane, or ceramic membrane.

The molecular sieve is 3 Å or 4 Å molecular sieve.

The lipase is an immobilized lipase or liquid lipase derived from *Candida antarctica*, *Thermomyces lanuginosus*, *Aspergillus niger*, *Rhizomucor miehei*, or *Rhizopus oryzae*.

The short chain alcohol is methanol, ethanol, propanol, or butanol.

The oil and fat is biological oil and fat, including vegetable oil, animal fat, waste cooking oil, oil and fat refining waste, or microbial oil.

The vegetable oil is castor oil, palm oil, colza oil, soybean oil, peanut oil, corn oil, cottonseed oil, rice bran oil, *Jatropha* oil, *Xanthoceras sorbifolia* oil, or *Jatropha curcas* L. oil.

The waste cooking oil refers to swill oil or drainage oil.

The oil and fat refining waste is acidified oil.

The animal fat is fish oil, tallow oil, lard oil, or mutton oil.

The microbial oil is yeast oil or microalgae oil.

The beneficial effects of the invention lie in that, in the single-step or multiple-step reaction process of enzyme catalysis, the acid value of the final biodiesel product can be less than 0.5 mg KOH per gram of oil by introducing online dehydration during the whole process or part of the process. Such online dehydration process greatly simplifies the operation procedure, and provides good economic and environmental benefits.

DESCRIPTION FOR THE DRAWINGS

SPECIFIC EMBODIMENTS

EXAMPLE 1

Figure 1:
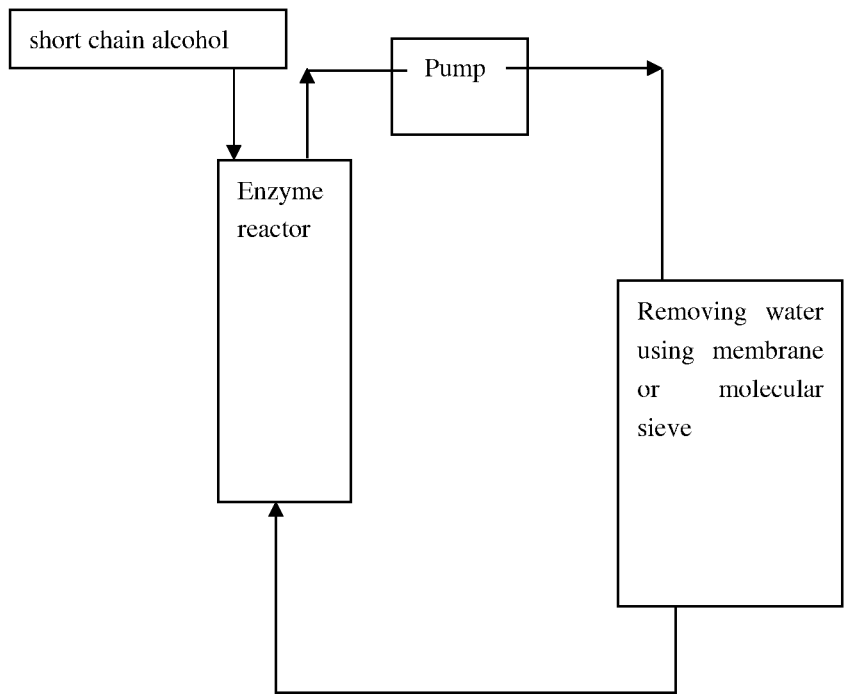
FIG. 1 is the schematic diagram for preparing biodiesel by single-stage enzymatic conversion of renewable oil and fat with online dehydration.

Methanol and colza oil with a molar ratio of 5:1 was placed in an enzymatic reactor, the system contained 0.5% water, 200 standard active units of immobilized lipase derived from *Aspergillus oryzae* based on the unit mass of oil and fat was added, the temperature was maintained at 40° C., and the methanol was evenly added within the first 3 hours. During the reaction process, the online dehydration as shown in FIG. 1 was conducted (membrane dehydration device including organic membrane, inorganic membrane, or ceramic membrane, and water-absorbing device including 3 Å or 4 Å molecular sieve). After 6 hours' reaction, the yield of fatty acid monoester in the system was higher than 98%, and the acid value is less than 0.5 mg KOH per gram of oil.

EXAMPLE 2

Ethanol and castor oil with a molar ratio of 6:1 was placed in an enzymatic reactor, the system contained 2% water, 300 standard active units of immobilized lipase derived from *Aspergillus oryzae* based on the unit mass of oil and fat was added, the temperature was maintained at 50° C., and the ethanol was evenly added within the first 3 hours. During the reaction process, the online dehydration as shown in FIG. 1 was conducted (membrane dehydration device including organic membrane, inorganic membrane, or ceramic membrane, and water-absorbing device including 3 Å or 4 Å molecular sieve). After 6 hours' reaction, the yield of fatty acid monoester in the system was higher than 98%, and the acid value is less than 0.5 mg KOH per gram of oil.

EXAMPLE 3

Figure 2:
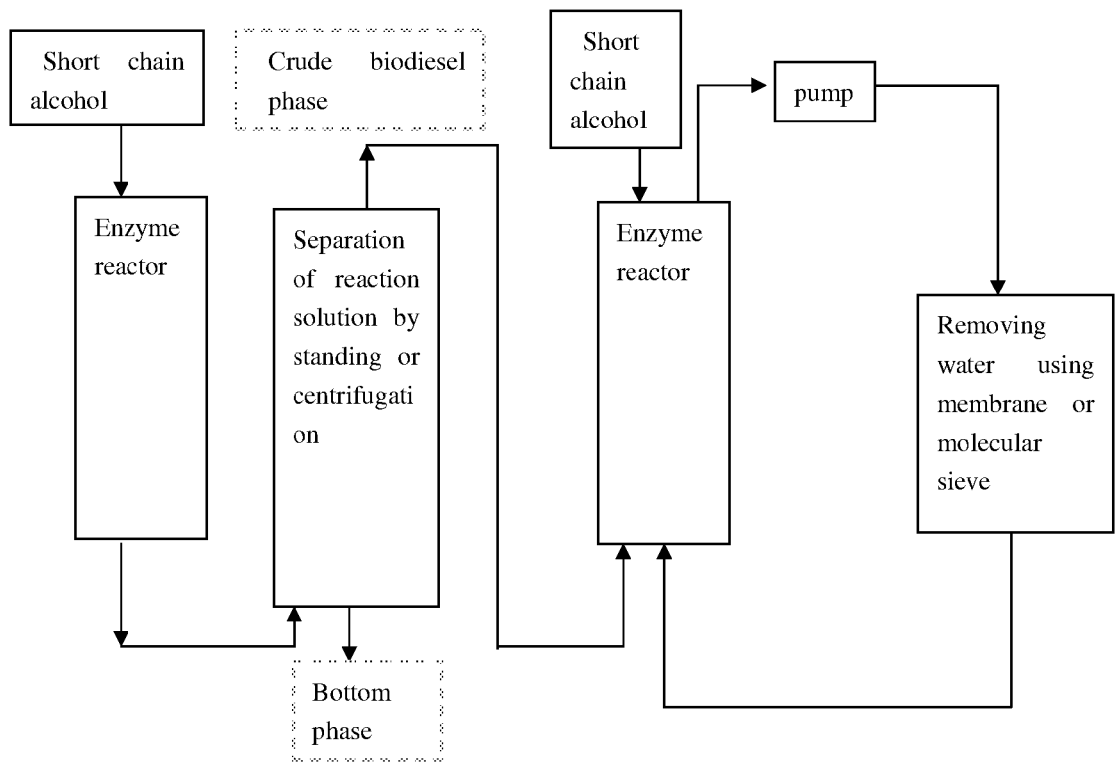
FIG. 2 is the schematic diagram for preparing biodiesel by multi-stage enzymatic conversion of renewable oil and fat with online dehydration.

Ethanol and soybean oil with a molar ratio of 4.5:1 was placed in an enzymatic reactor, the system contained 10% water, 200 standard active units of liquid lipase derived from *Candida antarctica* based on the unit mass of oil and fat was added, the temperature was maintained at 35° C., and the ethanol was evenly added within 5 hours. After the reaction was finished, standing or centrifugation was performed to separate glycerol phase and crude biodiesel phase. The crude biodiesel phase was then added into an enzymatic reactor for further reaction, methanol of a molar ratio of 1.5:1 based on the crude biodiesel was added, 200 standard active units of immobilized lipase derived from *Aspergillus oryzae* based on the unit mass of oil and fat was added, the temperature was maintained at 20° C., and the methanol was added within 2 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 5 hours' reaction, the yield of fatty acid monoester in the system was higher than 98%, and the acid value is less than 0.5mg KOH per gram of oil.

EXAMPLE 4

Methanol and lard oil with a molar ratio of 6:1 was placed in an enzymatic reactor, the system contained 5% water, 200 standard active units of liquid lipase derived from *Aspergillus oryzae* based on the unit mass of oil and fat was added, the temperature was maintained at 35° C., and the methanol was evenly added within 5 hours. After the reaction was finished, standing or centrifugation was performed to separate glycerol phase and crude biodiesel phase. The crude biodiesel phase was then added into an enzymatic reactor for further reaction, methanol of a molar ratio of 2:1 based on the crude biodiesel was added, 200 standard active units of immobilized lipase derived from *Aspergillus oryzae* based on the unit mass of oil and fat was added, the temperature was maintained at 20° C., and the methanol was added within 2 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 5 hours' reaction, the yield of fatty acid monoester in the system was higher than 98%, and the acid value is less than 0.5 mg KOH per gram of oil.

EXAMPLE 5

Ethanol and mutton oil with a molar ratio of 6:1 was placed in an enzymatic reactor, the system contained 2% water, 300 standard active units of immobilized lipase derived from *Aspergillus oryzae* based on the unit mass of oil and fat was added, the temperature was maintained at 40° C., and the methanol was evenly added within 5 hours. After the reaction was finished, standing or centrifugation was performed to separate glycerol phase and crude biodiesel phase. The crude biodiesel phase was then added into an enzymatic reactor for further reaction, methanol of a molar ratio of 1.5:1 based on the crude biodiesel was added, 200 standard active units of immobilized lipase derived from *Aspergillus oryzae* based on the unit mass of oil and fat was added, the temperature was maintained at 20° C., and the methanol was added within 2 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 5 hours' reaction, the yield of fatty acid monoester in the system was higher than 98%, and the acid value is less than 0.5 mg KOH per gram of oil.

EXAMPLE 6

Methanol and swill oil with a molar ratio of 4.5:1 was placed in an enzymatic reactor, the system contained 15% water, 200 standard active units of immobilized lipase derived from *Aspergillus oryzae* based on the unit mass of oil and fat was added, the temperature was maintained at 35° C., and the methanol was evenly added within 5 hours. After the reaction was finished, standing or centrifugation was performed to separate glycerol phase and crude biodiesel phase. The crude biodiesel phase was then added into an enzymatic reactor for further reaction, 50 standard active units of immobilized lipase derived from *Candida antarctica* based on the unit mass of oil and fat was placed in the reactor, methanol of 2:1 based on the crude biodiesel was added, and the methanol was added within 2 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 5 hours' reaction, the yield of fatty acid monoester in the system was higher than 98%, and the acid value is less than 0.5 mg KOH per gram of oil.

EXAMPLE 7

Methanol and cottonseed oil with a molar ratio of 5:1 was placed in an enzymatic reactor, the system contained 0.5% water, 1000 standard active units of immobilized lipase derived from *Rhizomucor miehei* based on the unit mass of oil and fat was added, the temperature was maintained at 40° C., and the methanol was evenly added within the first 3 hours. During the reaction process, the online dehydration as shown in FIG. 1 was conducted (membrane dehydration device including organic membrane, inorganic membrane, or ceramic membrane, and water-absorbing device including 3 Å or 4 Å molecular sieves). After 5 hours' reaction, the yield of fatty acid monoester in the system was higher than 98%, and the acid value is less than 0.5 mg KOH per gram of oil.

EXAMPLE 8

Ethanol and *Jatropha* oil with a molar ratio of 6:1 was placed in an enzymatic reactor, the system contained 2% water, 2000 standard active units of immobilized lipase derived from *Rhizopus oryzae* based on the unit mass of oil and fat was added, the temperature was maintained at 30° C., and the ethanol was evenly added within the first 2 hours. During the reaction process, the online dehydration as shown in FIG. 1 was conducted (membrane dehydration device including organic membrane, inorganic membrane, or ceramic membrane, and water-absorbing device including 3 Å or 4 Å molecular sieve). After 4 hours' reaction, the yield of fatty acid monoester in the system was higher than 98%, and the acid value is less than 0.5 mg KOH per gram of oil.

EXAMPLE 9

Ethanol and palm oil with a molar ratio of 6:1 was placed in an enzymatic reactor, the system contained 3% water, 800 standard active units of liquid lipase derived from *Thermomyces lanuginosus* based on the unit mass of oil and fat was added, the temperature was maintained at 45° C., and the ethanol was evenly added within 3 hours. After the reaction was finished, standing or centrifugation was performed to separate glycerol phase and crude biodiesel phase. The crude biodiesel phase was then added into an enzymatic reactor for further reaction, methanol of a molar ratio of 1:1 based on the crude biodiesel was added, 200 standard active units of immobilized lipase derived from *Aspergillus oryzae* based on the unit mass of oil and fat was added, the temperature was maintained at 20° C., and the propanol was added within 2 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 5 hours' reaction, the yield of fatty acid monoester in the system was higher than 98%, and the acid value is less than 0.5 mg KOH per gram of oil.

EXAMPLE 10

Methanol and yeast oil with a molar ratio of 4:1 was placed in an enzymatic reactor, the system contained 3% water, 400 standard active units of liquid lipase derived from *Candida antarctica* based on the unit mass of oil and fat was added, the temperature was maintained at 50° C., and the methanol was evenly added within 4 hours. After the reaction was finished, standing or centrifugation was performed to separate glycerol phase and crude biodiesel phase. The crude biodiesel phase was then added into an enzymatic reactor for further reaction, methanol of a molar ratio of 2:1 based on the crude biodiesel was added, 200 standard active units of immobilized lipase derived from *Aspergillus oryzae* based on the unit mass of oil and fat was added, the temperature was maintained at 20° C., and the methanol was added within 2 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 5 hours' reaction, the yield of fatty acid monoester in the system was higher than 98%, and the acid value is less than 0.5 mg KOH per gram of oil.

EXAMPLE 11

Ethanol and *Jatropha curcas* L. oil with a molar ratio of 6:1 was placed in an enzymatic reactor, the system contained 8% water, 800 standard active units of liquid lipase derived from *Candida antarctica* based on the unit mass of oil and fat was added, the temperature was maintained at 40° C., and the ethanol was evenly added within 3 hours. After the reaction was finished, standing or centrifugation was performed to separate glycerol phase and crude biodiesel phase. The crude biodiesel phase was then added into an enzymatic reactor for further reaction, methanol of a molar ratio of 1:1 based on the crude biodiesel was added, 200 standard active units of immobilized lipase derived from *Thermomyces lanuginosus* based on the unit mass of oil and fat was added, the temperature was maintained at 20° C., and the methanol was added within 2 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 5 hours' reaction, the yield of fatty acid monoester in the system was higher than 98%, and the acid value is less than 0.5 mg KOH per gram of oil.

EXAMPLE 12

Methanol and microalgae oil with a molar ratio of 4.5:1 was placed in an enzymatic reactor, the system contained 2% water, 2000 standard active units of immobilized lipase derived from *Aspergillus oryzae* based on the unit mass of oil and fat was added, the temperature was maintained at 35° C., and the methanol was evenly added within 2 hours. After the reaction was finished, standing or centrifugation was performed to separate glycerol phase and crude biodiesel phase. The crude biodiesel phase was then added into enzymatic reactor for further reaction, 20 standard active units of immobilized lipase derived from *Candida antarctica* based on the unit mass of oil and fat was placed in the reactor, methanol of 2:1 based on the crude biodiesel was added, and the methanol was added within 5 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 10 hours' reaction, the yield of fatty acid monoester in the system was higher than 98%, and the acid value is less than 0.5 mg KOH per gram of oil.

EXAMPLE 13

Ethanol and fish oil with a molar ratio of 6:1 was placed in an enzymatic reactor, the system contained 10% water, 500 standard active units of liquid lipase derived from *Rhizomu-*

*cor miehei* based on the unit mass of oil and fat was added, the temperature was maintained at 30° C., and the ethanol was evenly added within 5 hours. After the reaction was finished, standing or centrifugation was performed to separate glycerol phase and crude biodiesel phase. The crude biodiesel phase was then added into enzymatic reactor for further reaction, methanol of a molar ratio of 1.5:1 based on the crude biodiesel was added, 400 standard active units of immobilized lipase derived from *Aspergillus oryzae* based on the unit mass of oil and fat was added, the temperature was maintained at 20° C., and the methanol was added within 2 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 5 hours' reaction, the yield of fatty acid monoester in the system was higher than 98%, and the acid value is less than 0.5 mg KOH per gram of oil.

EXAMPLE 14

Methanol and corn oil with a molar ratio of 4:1 was placed in an enzymatic reactor, the system contained 1% water, 600 standard active units of immobilized lipase derived from *Aspergillus oryzae* based on the unit mass of oil and fat was added, the temperature was maintained at 50° C., and the methanol was evenly added within 3 hours. After the reaction was finished, standing or centrifugation was performed to separate glycerol phase and crude biodiesel phase. The crude biodiesel phase was then added into an enzymatic reactor for further reaction, methanol of a molar ratio of 2:1 based on the crude biodiesel was added, 200 standard active units of immobilized lipase derived from *Rhizomucor miehei* based on the unit mass of oil and fat was added, the temperature was maintained at 20° C., and the methanol was added within 4 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 6 hours' reaction, the yield of fatty acid monoester in the system was higher than 98%, and the acid value is less than 0.5 mg KOH per gram of oil.

EXAMPLE 15

Ethanol and swill oil with a molar ratio of 5:1 was placed in an enzymatic reactor, the system contained 6% water, 500 standard active units of liquid lipase derived from *Rhizomucor miehei* based on the unit mass of oil and fat was added, the temperature was maintained at 35° C., and the methanol was evenly added within 4 hours. After the reaction was finished, standing or centrifugation was performed to separate glycerol phase and crude biodiesel phase. The crude biodiesel phase was then added into enzymatic reactor for further reaction, methanol of a molar ratio of 1:1 based on the crude biodiesel was added, 100 standard active units of immobilized lipase derived from *Aspergillus oryzae* based on the unit mass of oil and fat was added, the temperature was maintained at 25° C., and the methanol was added within 5 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 7 hours' reaction, the yield of fatty acid monoester in the system was higher than 98%, and the acid value is less than 0.5 mg KOH per gram of oil.

EXAMPLE 16

Propanol and acidified oil with a molar ratio of 5:1 was placed in an enzymatic reactor, the system contained 3% water, 500 standard active units of liquid lipase derived from *Aspergillus oryzae* based on the unit mass of oil and fat was added, the temperature was maintained at 40° C., and the methanol was evenly added within 5 hours. After the reaction was finished, standing or centrifugation was performed to separate glycerol phase and crude biodiesel phase. The crude biodiesel phase was then added into an enzymatic reactor for further reaction, methanol of a molar ratio of 2:1 based on the crude biodiesel was added, 200 standard active units of immobilized lipase derived from *Aspergillus oryzae* based on the unit mass of oil and fat was added, the temperature was maintained at 20° C., and the methanol was added within 2 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 5 hours' reaction, the yield of fatty acid monoester in the system was higher than 98%, and the acid value is less than 0.5mg KOH per gram of oil.

EXAMPLE 17

Ethanol and castor oil with a molar ratio of 6:1 was placed in an enzymatic reactor, the system contained 8% water, 800 standard active units of liquid lipase derived from *Candida antarctica* based on the unit mass of oil and fat was added, the temperature was maintained at 45° C., and the ethanol was evenly added within 3 hours. After the reaction was finished, standing or centrifugation was performed to separate glycerol phase and crude biodiesel phase. The crude biodiesel phase was then added into an enzymatic reactor for further reaction, methanol of a molar ratio of 1:1 based on the crude biodiesel was added, 200 standard active units of immobilized lipase derived from *Candida antarctica* based on the unit mass of oil and fat was added, the temperature was maintained at 20° C., and the methanol was added within 2 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 5 hours' reaction, the yield of fatty acid monoester in the system was higher than 98%, and the acid value is less than 0.5 mg KOH per gram of oil.

EXAMPLE 18

Methanol and drainage oil with a molar ratio of 5:1 was placed in an enzymatic reactor, the system contained 12% water, 2000 standard active units of liquid lipase derived from *Aspergillus oryzae* based on the unit mass of oil and fat was added, the temperature was maintained at 35° C., and the methanol was evenly added within 2 hours. After the reaction was finished, standing or centrifugation was performed to separate glycerol phase and crude biodiesel phase. The crude biodiesel phase was then added into an enzymatic reactor for further reaction, 20 standard active units of immobilized lipase derived from *Candida antarctica* based on the unit mass of oil and fat was placed in the reactor, ethanol of 2:1 based on the crude biodiesel was added, and the ethanol was added within 5 hours; during the reaction process, the online dehydration as shown in FIG. 2 was conducted (membrane dehydration device including organic membrane, or ceramic membrane, and water-absorbing device including 3 Å or 4 Å molecular sieve). After 10 hours' reaction, the yield of fatty acid monoester in the system was higher than 98%, and the acid value is less than 0.5 mg KOH per gram of oil.

EXAMPLE 19

Ethanol and soybean oil with a molar ratio of 6:1 was placed in an enzymatic reactor, the system contained 2% water, 400 standard active units of immobilized lipase derived from *Aspergillus niger* based on the unit mass of oil and fat was added, the temperature was maintained at 30° C., and the ethanol was evenly added within the first 3 hours. During the reaction process, the online dehydration as shown in FIG. 1 was conducted (membrane dehydration device including organic membrane, inorganic membrane, or ceramic membrane, and water-absorbing device including 3 Å or 4 Å molecular sieve). After 6 hours' reaction, the yield of fatty acid monoester in the system was higher than 98%, and the acid value is less than 0.5 mg KOH per gram of oil.

EXAMPLE 20

Ethanol and mutton oil with a molar ratio of 5:1 was placed in an enzymatic reactor, the system contained 6% water, 1000 standard active units of liquid lipase derived from *Aspergillus niger* based on the unit mass of oil and fat was added, the temperature was maintained at 40° C., and the methanol was evenly added within 3 hours. After the reaction was finished, standing or centrifugation was performed to separate glycerol phase and crude biodiesel phase. The crude biodiesel phase was then added into an enzymatic reactor for further reaction, 100 standard active units of immobilized lipase derived from *Candida antarctica* based on the unit mass of oil and fat was placed in the reactor, methanol of 2:1 based on the crude biodiesel was added, and the methanol was added within 5 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 8 hours' reaction, the yield of fatty acid monoester in the system was higher than 98%, and the acid value is less than 0.5 mg KOH per gram of oil.

EXAMPLE 21

Methanol and swill oil with a molar ratio of 6:1 was placed in an enzymatic reactor, the system contained 12% water, 600 standard active units of liquid lipase derived from *Aspergillus niger* based on the unit mass of oil and fat was added, the temperature was maintained at 35° C., and the ethanol was evenly added within 3 hours. After the reaction was finished, standing or centrifugation was performed to separate glycerol phase and crude biodiesel phase. The crude biodiesel phase was then added into an enzymatic reactor for further reaction, methanol of a molar ratio of 2:1 based on the crude biodiesel was added, 200 standard active units of immobilized lipase derived from *Rhizomucor miehei* based on the unit mass of oil and fat was added, the temperature was maintained at 20° C., and the methanol was added within 4 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 6 hours' reaction, the yield of fatty acid monoester in the system was higher than 98%, and the acid value is less than 0.5 mg KOH per gram of oil.

EXAMPLE 22

Ethanol and *Jatropha curcas* L. oil with a molar ratio of 6:1 was placed in an enzymatic reactor, the system contained 8% water, 500 standard active units of liquid lipase derived from *Thermomyces lanuginosus* based on the unit mass of oil and fat was added, the temperature was maintained at 45° C., and the ethanol was evenly added within 4 hours. After the reaction was finished, standing or centrifugation was performed to separate glycerol phase and crude biodiesel phase. The crude biodiesel phase was then added into an enzymatic reactor for further reaction, methanol of a molar ratio of 1:1 based on the crude biodiesel was added, 200 standard active units of immobilized lipase derived from *Candida antarctica* based on the unit mass of oil and fat was added, the temperature was maintained at 25° C., and the methanol was added within 2 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 5 hours' reaction, the yield of fatty acid monoester in the system was higher than 98%, and the acid value is less than 0.5 mg KOH per gram of oil.

EXAMPLE 23

Methanol and microalgae oil with a molar ratio of 5:1 was placed in an enzymatic reactor, the system contained 1% water, 1500 standard active units of immobilized lipase derived from *Thermomyces lanuginosus* based on the unit mass of oil and fat was added, the temperature was maintained at 50° C., and the methanol was evenly added within 2 hours. After the reaction was finished, standing or centrifugation was performed to separate glycerol phase and crude biodiesel phase. The crude biodiesel phase was then added into an enzymatic reactor for further reaction, 100 standard active units of immobilized lipase derived from *Candida antarctica* based on the unit mass of oil and fat was placed in the reactor, methanol of 1:1 based on the crude biodiesel was added, and the methanol was added within 2 hours; during the reaction process, the online dehydration as shown in FIG. 2 was conducted (membrane dehydration device including organic membrane, inorganic membrane, or ceramic membrane, and water-absorbing device including 3 Å or 4 Å molecular sieve). After 8 hours' reaction, the yield of fatty acid monoester in the system was higher than 98%, and the acid value is less than 0.5 mg KOH per gram of oil.

EXAMPLE 24

Ethanol and castor oil with a molar ratio of 6:1 was placed in an enzymatic reactor, the system contained 0.8% water, 100 standard active units of immobilized lipase derived from *Aspergillus niger* and 200 standard active unit of immobilized lipase derived from *Thermomyces lanuginosus* based on the unit mass of oil and fat were added, the temperature was maintained at 45° C., and the ethanol was evenly added within the first 2 hours. During the reaction process, the online dehydration as shown in FIG. 1 was conducted (membrane dehydration device including organic membrane, inorganic membrane, or ceramic membrane, and water-absorbing device including 3 Å or 4 Å molecular sieve). After 5 hours' reaction, the yield of fatty acid monoester in the system was higher than 98%, and the acid value is less than 0.5 mg KOH per gram of oil.

The invention claimed is:

1. A process for preparing biodiesel from renewable oil and fat catalyzed by lipase with online dehydration, wherein a short chain alcohol ROH is used as an acyl-acceptor, and a lipase is utilized as the catalyst to catalyze transesterification reaction of oil and fat feedstock with said short chain alcohol, so as to synthesize biodiesel comprising the steps of:
   adding oil and fat in a single-stage or multi-stage reactor,
   adding 4-8 mole of short chain alcohol per mole of the oil and fat, and 20-2000 active units of lipase per gram of the oil and fat into the reactor, wherein one unit of lipase produces one μmol of the product per minute,
   carrying out online dehydration with a membrane or a molecular sieve during the whole or part of the catalytic process by the lipase; and
   maintaining the temperature at 20-50° C.;
   after 3-10 hours reaction, the yield for converting oil and fat feedstock into biodiesel being over 98%, and the final product requiring less than 0.5 mg KOH per gram of oil to neutralize.

2. The process according to claim 1, wherein said online dehydration with a membrane or a molecular sieve carried out during the whole process is online dehydration with a membrane or a molecular sieve carried out during the whole process or part of the reaction process of enzyme catalysis.

3. The process according to claim 1, wherein the membrane is an organic membrane, an inorganic membrane, or a ceramic membrane.

4. The process according to claim 1, wherein the molecular sieve is 3 Angstrom or 4 Angstrom in diameter.

5. The process according to claim 1, wherein the lipase is immobilized lipase or liquid lipase derived from *Candida antarctica, Thermomyces lanuginosus, Aspergillus niger, Rhizomucor miehei*, or *Rhizopus oryzae*.

6. The process according to claim 1, wherein the short chain alcohol is methanol, ethanol, propanol, or butanol.

7. The process according to claim 1, wherein the oil and fat is biological oil and fat, including vegetable oil, animal fat, waste cooking oil, oil and fat refining waste, or microbial oil.

8. The process according to claim 7, wherein the vegetable oil is castor oil, palm oil, colza oil, soybean oil, peanut oil, corn oil, cottonseed oil, rice bran oil, *Jatropha* oil, or *Jatropha curcas* L. oil.

9. The process according to claim 7, wherein the waste cooking oil includes swill oil or drainage oil; and the oil and fat refining waste is acidified oil.

10. The process according to claim 7, wherein the animal fat includes fish oil, tallow, lard, or mutton oil; and the microbial oil includes yeast oil or microalgae oil.

* * * * *